US010278680B2

(12) United States Patent
Costello et al.

(10) Patent No.: US 10,278,680 B2
(45) Date of Patent: May 7, 2019

(54) DEVICES, SYSTEMS, AND METHODS FOR NAVIGATING A BIOPSY TOOL TO A TARGET LOCATION AND OBTAINING A TISSUE SAMPLE USING THE SAME

(71) Applicant: COVIDIEN LP, Mansfield, MA (US)

(72) Inventors: David M. Costello, Delano, MN (US); Thomas P. Crowley, Lino Lakes, MN (US); Thomas D. Magnuson, Plymouth, MN (US)

(73) Assignee: COVIDIEN LP, Mansfield, MA (US)

( * ) Notice: Subject to any disclaimer, the term of this patent is extended or adjusted under 35 U.S.C. 154(b) by 509 days.

(21) Appl. No.: 14/564,779

(22) Filed: Dec. 9, 2014

(65) Prior Publication Data

US 2015/0265257 A1    Sep. 24, 2015

Related U.S. Application Data

(60) Provisional application No. 61/955,407, filed on Mar. 19, 2014.

(51) Int. Cl.
*A61B 10/04* (2006.01)
*A61B 10/02* (2006.01)
(Continued)

(52) U.S. Cl.
CPC ............ *A61B 10/04* (2013.01); *A61B 1/2676* (2013.01); *A61B 5/065* (2013.01); *A61B 10/0266* (2013.01); *A61B 10/0275* (2013.01); *A61B 34/20* (2016.02); *A61B 2034/107* (2016.02); *A61B 2034/2051* (2016.02)

(58) Field of Classification Search
CPC . A61B 10/0266; A61B 10/0275; A61B 10/04; A61B 1/2676; A61B 2034/107; A61B 2034/2051; A61B 34/20; A61B 5/065
See application file for complete search history.

(56) References Cited

U.S. PATENT DOCUMENTS

| 3,844,272 A | 10/1974 | Banko |
| 3,882,849 A | 5/1975 | Jamshidi |

(Continued)

FOREIGN PATENT DOCUMENTS

| CN | 102231965 A | 11/2011 |
| CN | 102860841 A | 1/2013 |

(Continued)

OTHER PUBLICATIONS

European Search Report Application No. EP14200553, dated Jun. 15, 2015, 6 pages.

(Continued)

*Primary Examiner* — Michael T Rozanski

(57) ABSTRACT

A system for performing a surgical procedure includes a bronchoscope, monitoring equipment coupled to the bronchoscope, a tracking system, a positioning assembly, and a biopsy tool. The biopsy tool includes an elongated flexible body extending from a proximal end to a distal end and a biopsy member formed on the distal end of the elongated flexible body. The biopsy member includes a tissue-receiving portion defining an opening including sharpened edges. The sharpened edges are disposed on the interior perimeter of the opening and are capable of cutting tissue. A biopsy tool is also provided.

20 Claims, 12 Drawing Sheets

(51) Int. Cl.
*A61B 1/267* (2006.01)
*A61B 5/06* (2006.01)
*A61B 34/20* (2016.01)
*A61B 34/10* (2016.01)

(56) References Cited

U.S. PATENT DOCUMENTS

| | | | |
|---|---|---|---|
| 4,111,207 A | 9/1978 | Seiler, Jr. |
| 4,177,797 A | 12/1979 | Baylis et al. |
| 4,662,869 A | 5/1987 | Wright |
| 4,682,606 A | 7/1987 | DeCaprio |
| 4,702,260 A | 10/1987 | Wang |
| 4,708,147 A | 11/1987 | Haaga |
| 5,251,641 A | 10/1993 | Xavier |
| 5,615,690 A | 4/1997 | Giurtino et al. |
| 5,807,282 A | 9/1998 | Fowler |
| 6,083,237 A | 7/2000 | Huitema et al. |
| 6,162,214 A | 12/2000 | Mueller et al. |
| 6,709,408 B2 | 3/2004 | Fisher |
| 6,743,245 B2 | 6/2004 | Lobdell |
| 6,773,443 B2 | 8/2004 | Truwit et al. |
| 6,872,185 B2 | 3/2005 | Fisher |
| 6,890,309 B2 | 5/2005 | Fisher |
| 6,908,440 B2 | 6/2005 | Fisher |
| 6,981,949 B2 | 1/2006 | Hibner et al. |
| 7,189,206 B2 | 3/2007 | Quick et al. |
| 7,555,330 B2 | 6/2009 | Gilboa et al. |
| 7,969,143 B2 | 6/2011 | Gilboa |
| 7,998,062 B2 | 8/2011 | Gilboa |
| 8,241,225 B2 | 8/2012 | Seiger et al. |
| 8,262,585 B2 | 9/2012 | Thompson et al. |
| 8,343,072 B2 | 1/2013 | Bacon et al. |
| 8,343,073 B2 | 1/2013 | Miller |
| 8,506,503 B2 | 8/2013 | Fritscher-Ravens et al. |
| 8,532,748 B2 | 9/2013 | Leimbach et al. |
| 8,568,334 B2 | 10/2013 | Field et al. |
| 8,611,984 B2 | 12/2013 | Greenburg et al. |
| 8,641,640 B2 | 2/2014 | Lubock et al. |
| 8,784,333 B2 | 7/2014 | Corvi et al. |
| 8,821,411 B2 | 9/2014 | Berberich |
| 8,858,461 B2 | 10/2014 | Persat |
| 2007/0293721 A1 | 12/2007 | Gilboa |
| 2009/0284255 A1 | 11/2009 | Zur |
| 2010/0016757 A1 | 1/2010 | Greenburg et al. |
| 2010/0241028 A1 | 9/2010 | Johnson et al. |
| 2013/0046316 A1 | 2/2013 | Sullivan et al. |
| 2013/0223702 A1 | 8/2013 | Holsing et al. |
| 2013/0331733 A1 | 12/2013 | Plishka et al. |

FOREIGN PATENT DOCUMENTS

| | | |
|---|---|---|
| EP | 2018112 A2 | 1/2009 |
| WO | 00/10456 A1 | 3/2000 |
| WO | 2007109418 A2 | 9/2007 |
| WO | 2010004570 A1 | 1/2010 |

OTHER PUBLICATIONS

European Office Action dated Oct. 5, 2017 issued in corresponding European Application No. 14200553.7.
Chinese Office Action dated Feb. 2, 2019 issued in corresponding CN Appln. No. 201410850624.2.

DEVICES, SYSTEMS, AND METHODS FOR NAVIGATING A BIOPSY TOOL TO A TARGET LOCATION AND OBTAINING A TISSUE SAMPLE USING THE SAME

CROSS-REFERENCE TO RELATED APPLICATIONS

This application claims the benefit of, and priority to, U.S. Provisional Patent Appln. No. 61/955,407, filed on Mar. 19, 2014, the entire contents of which are incorporated herein by reference.

BACKGROUND

Technical Field

The present disclosure relates to biopsy sampling and, more particularly, to devices, systems, and methods for navigating a biopsy tool to a target location and obtaining a tissue sample using the biopsy tool.

Description of Related Art

A bronchoscope is inserted into a patient's airways through the patient's nose or mouth. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools and/or therapeutic instruments such as ablation probes, can be inserted.

Bronchoscopes are limited in how far they may be advanced through the airways due to their size. Where the bronchoscope is too large to reach a target location deep in the lungs, a locatable guide ("LG") enveloped by a sheath is often utilized to navigate from the end of the bronchoscope to the target location. That is, the LG, together with a navigation system, enables the position and orientation of the LG to be tracked as the LG is advanced through the airways.

In use, the LG/sheath combination is inserted through the working channel of the bronchoscope and into the patient's airways. Once the LG has been navigated to the target location, aided by the position and orientation tracking provided by the navigation system, the LG is retracted through the sheath, leaving the sheath in position. With the LG retracted, the sheath is often referred to as an extended working channel ("EWC") because it effectively functions as an extension of the working channel of the bronchoscope.

Once the LG has been retracted from the EWC, the EWC may be used as an avenue for guiding working tools, e.g., biopsy tools, ablation probes, etc., to the target location. However, once the LG is removed from the EWC, tracking is no longer provided and, thus, the operator is operating blind, relying on the EWC to remain fixed at the target location. Repositioning of the working tool at the target location is likewise required to be performed without guidance.

SUMMARY

A system for performing a surgical procedure provided in accordance with the present disclosure includes a bronchoscope, monitoring equipment coupled to the bronchoscope, a tracking system, a positioning assembly, and a biopsy tool. The biopsy tool includes an elongated flexible body extending from a proximal end to a distal end and a biopsy member formed on a distal end of the elongated flexible body. The biopsy member includes a tissue-receiving portion defining an opening including sharpened edges. The sharpened edges are disposed on the interior perimeter of the opening and are capable of cutting tissue.

In aspects, the biopsy member includes a sensor assembly including at least one location sensor. The location sensor is configured to enable detection of a location of the sensor assembly within a patient's airways.

In some aspects, the system includes a computer configured to execute software to facilitate navigation of a EWC to a target.

In certain aspects, the opening includes first and second longitudinally extending faces. The first and second longitudinally extending faces are disposed on either side of the opening and are angled inwardly and towards one another to define an acute interior angle therebetween. Each face includes a sharpened cutting edge disposed on either side of the opening and are positioned such that the sharpened cutting edges increasingly approximate one another in a distal to proximal direction culminating at an apex joint.

In aspects, the biopsy member defines a body separate from the elongated flexible body of the biopsy tool. The biopsy member is secured to the distal end of the elongated flexible body.

In some aspects, the biopsy member defines a generally hollow interior. The hollow interior is in fluid communication with the opening of the tissue receiving portion of the biopsy member.

In certain aspects, the biopsy tool is configured to connect to a vacuum source capable of applying suction at the biopsy member.

In aspects, the opening of the tissue receiving portion of the biopsy member is configured to capture tissue of a patient when the vacuum source is applied to the biopsy tool.

In some aspects, the tracking system includes a tracking module, a plurality of reference sensors, and a transmitter mat.

In certain aspects, the positioning assembly includes a locatable guide, an extended working channel, and a handle. The locatable guide includes a steerable distal tip and a sensor disposed within the distal tip. The locatable guide and the extended working channel are dimensioned for insertion through a working channel defined through the bronchoscope.

According to another aspect of the present disclosure, a biopsy tool includes an elongated flexible body defining a distal end. The distal end includes a biopsy member including a tissue-receiving portion. The tissue-receiving portion defines an opening including sharpened edges disposed on the interior perimeter of the opening capable of cutting tissue.

In aspects, the biopsy member includes a sensor assembly including at least one location sensor. The location sensor is configured to enable detection of a location of the sensor assembly within a patient's airways.

In some aspects, the opening includes first and second longitudinally extending faces disposed on either side of the opening. The first and second longitudinally-extending faces are angled inwardly and towards one another to define an acute interior angle therebetween. Each face includes a sharpened cutting edge disposed on either side of the opening. The first and second faces are positioned such that the sharpened cutting edges increasingly approximate one another in a distal to proximal direction culminating at an apex joint.

In certain aspects, the biopsy tool includes a proximal handle portion coupled to a proximal end of the elongated flexible body. The proximal handle portion is configured for manual manipulation to drive rotation of the screw member.

In aspects, the biopsy member defines a generally hollow interior. The hollow interior is in fluid communication with the opening of the tissue receiving portion of the biopsy member.

In some aspects, the biopsy tool is configured to connect to a vacuum source capable of applying suction at the biopsy member.

In certain aspects, the opening of the tissue receiving portion of the biopsy member is configured to capture tissue of a patient when the vacuum source is applied to the biopsy tool.

In aspects, the tissue receiving portion is defined by one or more plates.

In some aspects, the distal end of the biopsy member defines a generally blunt configuration.

In certain aspects, the biopsy member defines a body separate from the elongated flexible body of the biopsy tool which is fixedly secured thereto.

BRIEF DESCRIPTION OF THE DRAWINGS

Various aspects and features of the present disclosure are described hereinbelow with references to the drawings, wherein.

DETAILED DESCRIPTION

Devices, systems, and methods for navigating a biopsy tool to a target location and obtaining a tissue sample using the biopsy tool are provided in accordance with the present disclosure and described in detailed below. The various biopsy tools of the present disclosure, for example, each generally include a flexible body, a biopsy member disposed at the distal end of the flexible body, and a sensor assembly integrated into the biopsy tool and positioned adjacent the biopsy member. The biopsy member is configured to facilitate obtaining a tissue sample. The sensor assembly enables determination of the current location of the biopsy member, thus facilitating navigation of the biopsy member to target tissue and/or manipulation of the biopsy member relative to target tissue. However, it is also envisioned that the biopsy member be provided without the sensor assembly, depending on a particular purpose. Detailed embodiments of such devices, systems incorporating such devices, and methods using the same as described below. However, these detailed embodiments are merely examples of the present disclosure, which may be embodied in various forms.

Figure 1:
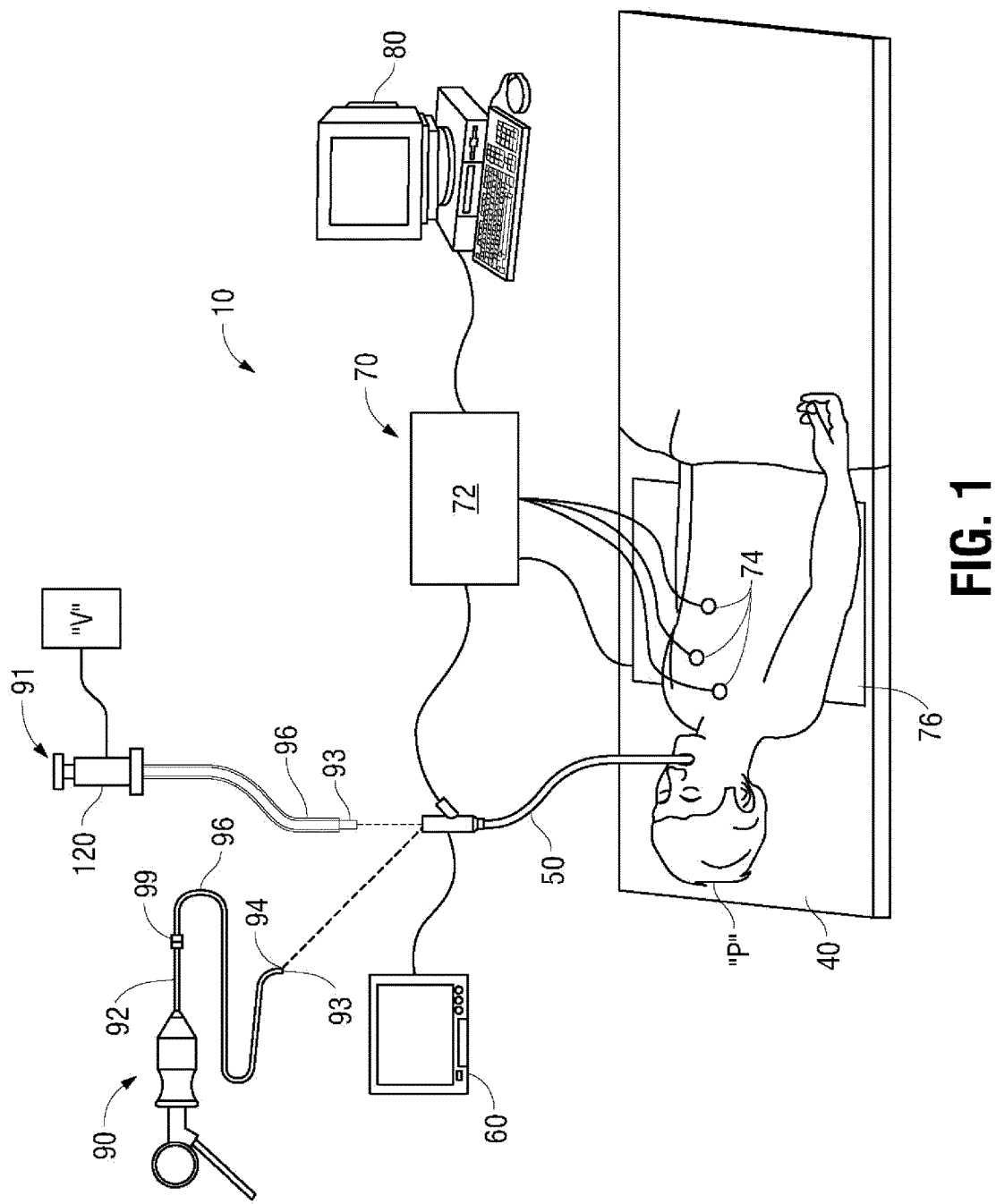
FIG. 1 is a perspective view of a system provided in accordance with the present disclosure configured for navigating a biopsy tool to a target location and obtaining a tissue sample using the biopsy tool.
Figure 2:
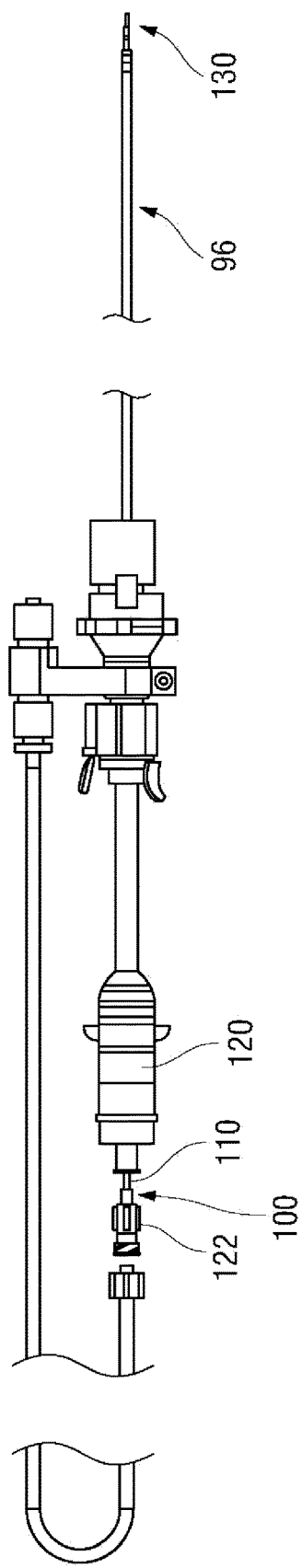
FIG. 2 is a side view of a biopsy tool, provided in accordance with the present disclosure and configured for use with the system of FIG. 1, showing a bronchial aspiration attachment including an extended working channel and biopsy catheter.

With reference to FIGS. 1 and 2, a system provided in accordance with the present disclosure and configured for planning a pathway to target tissue (planning phase), navigating a positioning assembly to the target tissue (navigation phase), and navigating a biopsy tool to the target tissue to obtain a tissue sample from the target tissue using the biopsy tool (biopsy phase) is shown generally identified by reference numeral 10. System 10 generally includes an operating table 40 configured to support a patient "P;" a bronchoscope 50 configured for insertion through the patient's mouth into the patient's airways; monitoring equipment 60 coupled to bronchoscope 50 for displaying video images received from bronchoscope 50; a tracking system 70 including a tracking module 72, a plurality of reference sensors 74, and a transmitter mat 76; a computer 80 including software and/or hardware used to facilitate pathway planning, identification of target tissue, and navigation to target tissue; a positioning assembly 90 or 91 including a locatable guide (LG) 92 an extended working channel (EWC) 96; and a biopsy tool 100 insertable through the positioning assembly 90, 91 and operable to obtain a tissue sample, e.g., for subsequent diagnostic testing. The planning and navigation phases will initially be detailed below, followed by a detailed description of biopsy tools provided in accordance with the present disclosure and use of such biopsy tools in conjunction with system 10 in performing the biopsy phase.

With respect to the planning phase, computer 80 utilizes computed tomographic (CT) image data for generating and viewing a three-dimensional model of the patient's airways, enables the identification of target tissue on the three-dimensional model (automatically, semi-automatically or manually), and allows for the selection of a pathway through the patient's airways to the target tissue. More specifically, the CT scans are processed and assembled into a three-dimensional CT volume, which is then utilized to generate a three-dimensional model of the patient's airways. The three-dimensional model may be displayed on a display monitor associated with computer 80, or in any other suitable fashion. Using computer 80, various views of the three-dimensional model may be provided and/or the three-dimensional model may be manipulated to facilitate identification of target tissue on the three-dimensional model and selection of a suitable pathway through the patient's airways to access the target tissue. Once selected, the pathway is saved for use during the navigation phase(s).

Continuing with reference to FIG. 1, patient "P" is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

With respect to the navigation phase, a six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or other suitable positioning measuring system, is utilized for performing registration and navigation, although other configurations are also contemplated. Tracking system 70 includes a tracking module 72, a plurality of reference sensors 74, and a transmitter mat 76. Tracking system 70 is configured for use with either positioning assembly 90 or positioning assembly 91, and biopsy tool 100, as detailed below. Positioning assemblies 90 and 91 include a LG 92 having a distal tip 93, which may be steerable. Positioning assemblies 90 and 91 further include an EWC 96 and a handle 98. LG 92 and EWC 96 are configured for insertion through a working channel of bronchoscope 50 into the patient's airways (although LG 92 and EWC 96 may alternatively be used without bronchoscope 50) and are selectively lockable relative to one another via a locking mechanism 99. Distal tip 93 of LG 92 may be configured for steering in any suitable fashion, e.g., using a plurality of steering wires (not shown) coupled between handle 98 and distal tip 93, to facilitate maneuvering distal tip 93 of LG 92 and EWC 96 through the patient's airways. Alternatively, rotation and translation of handle 120 may facilitate maneuvering of the distal tip 93 of LG 92, and in particular embodiments the EWC 96 may be angled or curved to assist in maneuvering the distal tip 93 through the airways. Sensor 94 is integrated with distal tip 93 of LG 92 and allows monitoring of the position and orientation of distal tip 93, in six degrees of freedom, relative to the reference coordinate system. Sensor 94 of LG 92 may be configured similar to any of the sensors detailed below (see FIGS. 6-8).

Figure 12:
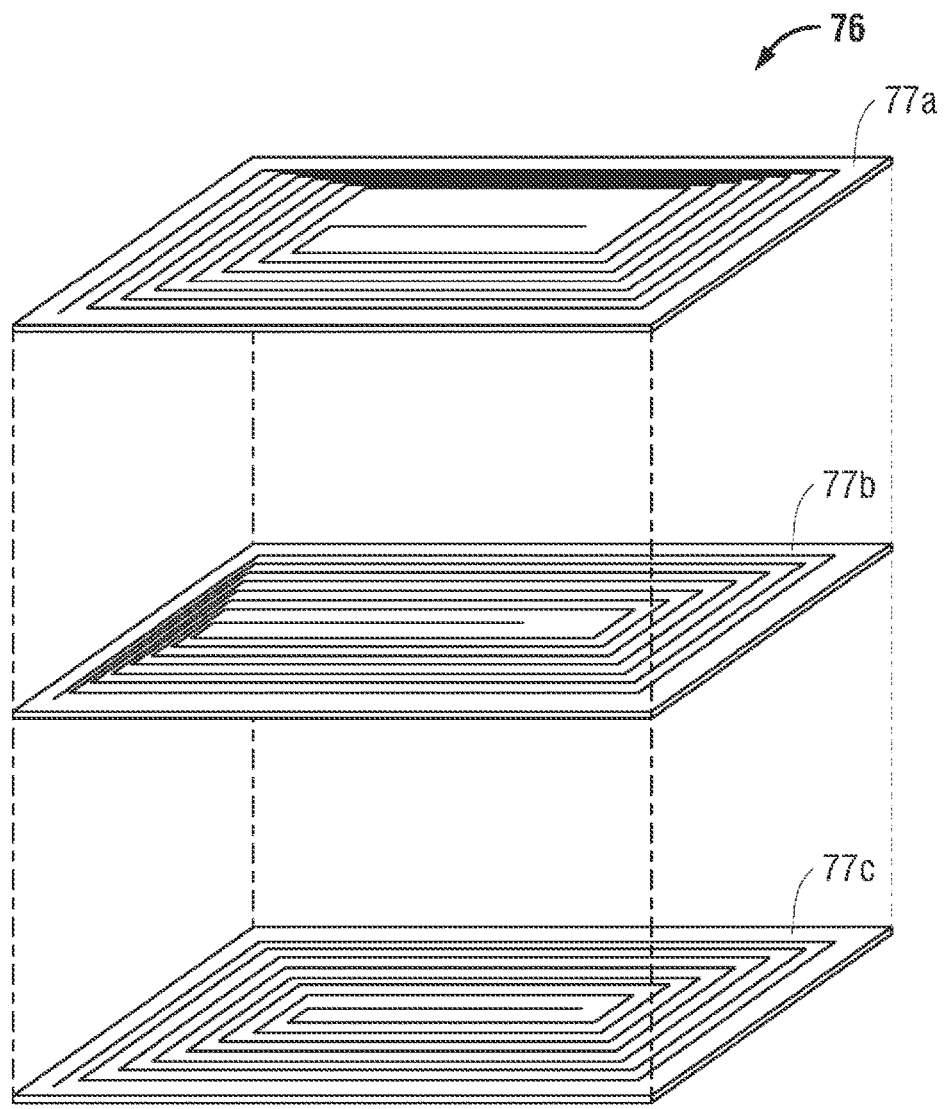
FIG. 12 is an exploded, perspective view of a transmitter mat configured for use with the system of FIG. 1 for tracking a biopsy tool through a patient's airways.

As shown in FIG. 1, transmitter mat 76 is positioned beneath patient "P." With additional reference to FIG. 12, an embodiment of the internal configuration of transmitter mat 76 of tracking system 70 (FIG. 1) is shown, although other suitable configurations are also contemplated. Transmitter mat 76 is a transmitter of electromagnetic radiation and includes a stack of three substantially planar rectangular loop antennas 77a, 77b, 77c configured to be connected to drive circuitry (not shown). For a detailed discussion of the construction of exemplary transmitter mats, which may also be referred to as location boards, reference may be made to U.S. Patent Application Publication No. 2009/0284255, filed Apr. 2, 2009, the entire contents of which are incorporated herein by reference.

Transmitter mat 76 and the plurality of reference sensors 74 are interconnected with tracking module 72, which derives the location of each sensor 74 in six degrees of freedom. One or more of reference sensors 74 are attached to the chest of the patient "P." The six degrees of freedom coordinates of reference sensors 74 are sent to computer 80 (which includes the appropriate software) where they are used to calculate a patient coordinate frame of reference. Registration, as detailed below, is generally performed by identifying locations in both the three-dimensional model and the patient's airways and measuring the coordinates in both systems. Further details of such a registration technique can be found in U.S. Patent Application Pub. No. 2011/0085720, the entire contents of which are incorporated herein by reference, although other suitable registration techniques are also contemplated.

In use, with respect to the navigation phase, LG 92 is inserted into positioning assembly 90, 91 and EWC 96 such that sensor 94 projects from the distal end of EWC 96. LG 92 and EWC 96 are then locked together via locking mechanism 99 (for example). LG 92, together with EWC 96, are then inserted through bronchoscope 50 and into the airways of the patient "P," with LG 92 and EWC 96 moving in concert with one another through bronchoscope 50 and into the airways of the patient "P." Automatic registration is performed by moving LG 92 through the airways of the patient "P." More specifically, data pertaining to locations of sensor 94 while LG 92 is moving through the airways is recorded using transmitter mat 76, reference sensors 74, and tracking module 72. A shape resulting from this location data is compared to an interior geometry of passages of the three-dimensional model generated in the planning phase, and a location correlation between the shape and the three-dimensional model based on the comparison is determined, e.g., utilizing the software on computer 80. In addition, the software identifies non-tissue space (e.g., air filled cavities) in the three-dimensional model. The software aligns, or registers, an image representing a location of sensor 94 of LG 92 with an image of the three-dimensional model based on the recorded location data and an assumption that LG 92 remains located in non-tissue space in the patient's airways. This completes the registration portion of the navigation phase.

Referring still to FIG. 1, once the planning phase has been completed, e.g., the target tissue has been identified and the pathway thereto selected, and registration has been completed, system 10 may be utilized to navigate LG 92 through the patient's airway to the target tissue. To facilitate such navigation, computer 80, monitoring equipment 60, and/or any other suitable display may be configured to display the three-dimensional model including the selected pathway from the current location of sensor 94 of LG 92 to the target tissue. Navigation of LG 92 to the target tissue using tracking system 70 is similar to that detailed below with respect to the navigation of biopsy tool 100 to the target tissue and, thus, is not detailed here for purposes of brevity.

Once LG 92 has been successfully navigated to the target tissue, completing the navigation phase, LG 92 may be unlocked from EWC 96 and removed, leaving EWC 96 in place as a guide channel for guiding biopsy tool 100 to the target tissue. Details of various embodiments of biopsy tools, along with the use of the same in the biopsy phase, are described below.

Referring now to FIG. 2, in conjunction with FIG. 1, one embodiment of a biopsy tool provided in accordance with the present disclosure for obtaining a tissue sample from the target tissue is shown generally identified by reference numeral 100. As detailed below, biopsy tool 100 is depicted inserted into navigation assembly 91 and further configured for use in conjunction with tracking system 70 to facilitate navigation of biopsy tool 100 to the target tissue and/or tracking of biopsy tool 100 as it is manipulated relative to the target tissue to obtain the tissue sample. Although registration and navigation are detailed above with respect to LG 92 of positioning assembly 90, 91, it is also envisioned that LG 92 be eliminated and biopsy tool 100 itself is utilized for registration and navigation, similarly as detailed above with respect to LG 92.

Figure 2A:
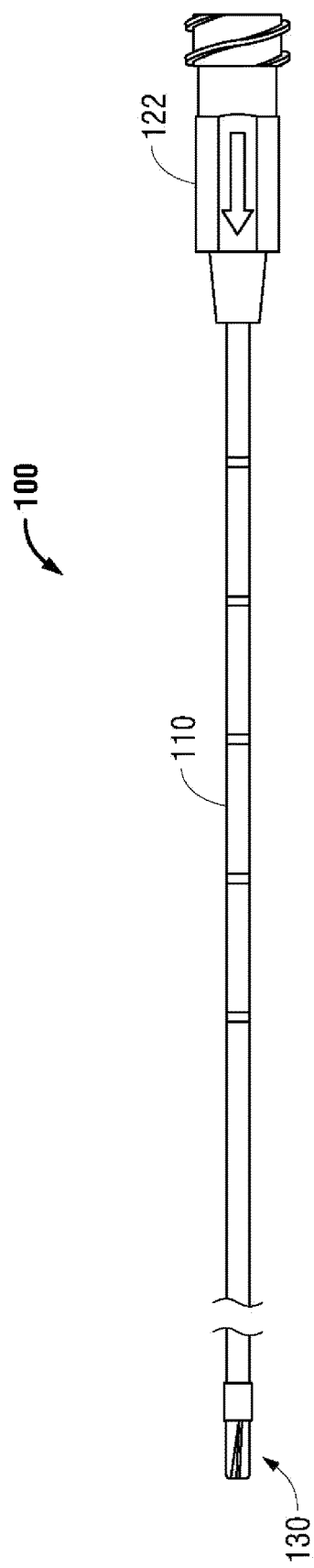
FIG. 2A is a side view of the biopsy tool of FIG. 2.

Biopsy tool 100, as best shown in FIG. 2A, in conjunction with FIGS. 1 and 2, generally includes an elongated flexible body 110 and a connector (122) securing the biopsy tool to the handle 120 of the navigation assembly 91. Connector 122 may include a vacuum source connector such as luer lock which fluidly connects the vacuum source to the biopsy tool 100. Flexible body 110 is configured to enable insertion of biopsy tool 100 into a patient's airways, e.g., through bronchoscope 50 and EWC 96 to the target tissue.

Figure 3:
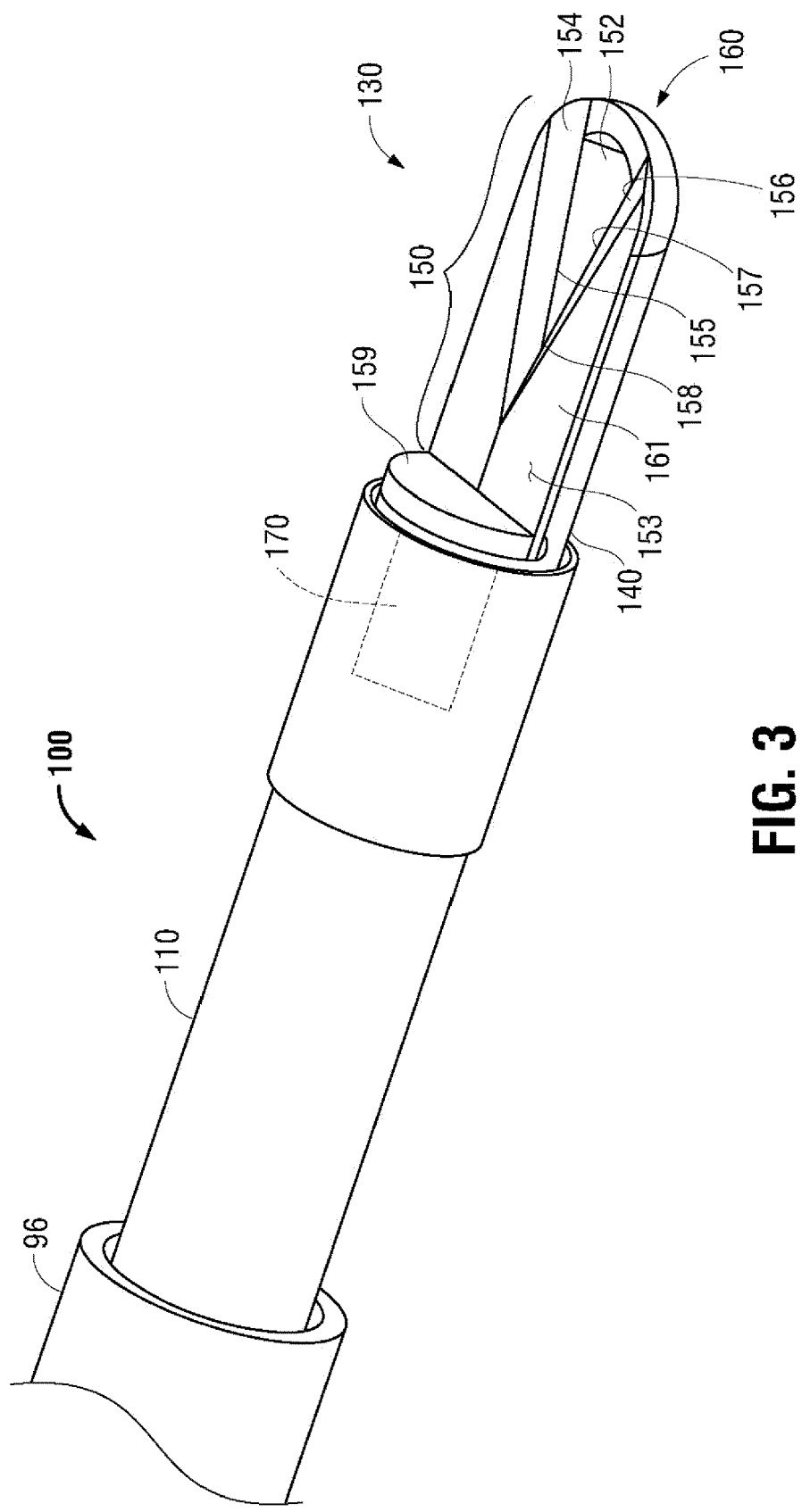
FIG. 3 is a perspective view of the distal end of a biopsy tool provided in accordance with the present disclosure and configured for use with the system of FIG. 1.
Figure 3A:
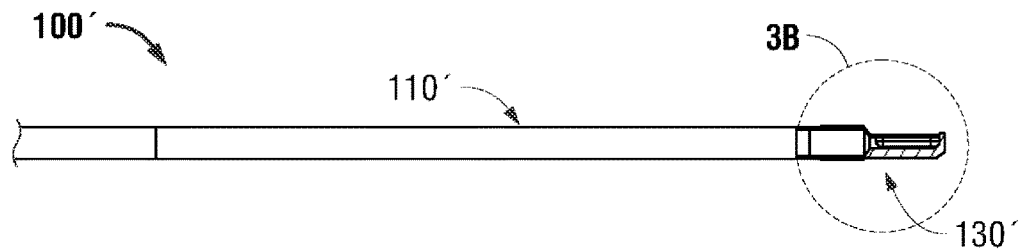
FIG. 3A is a side view of another biopsy tool provided in accordance with the present disclosure and configured for use with the system of FIG. 1.
Figure 3B:
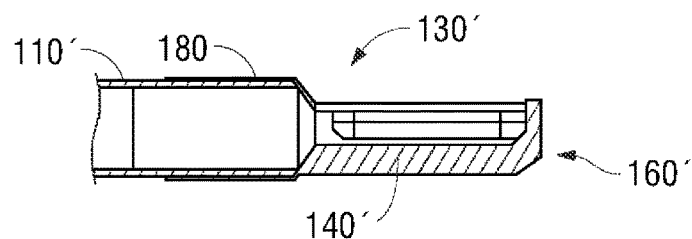
FIG. 3B is an enlarged view of the area of detail of FIG. 3A.
Figure 3C:
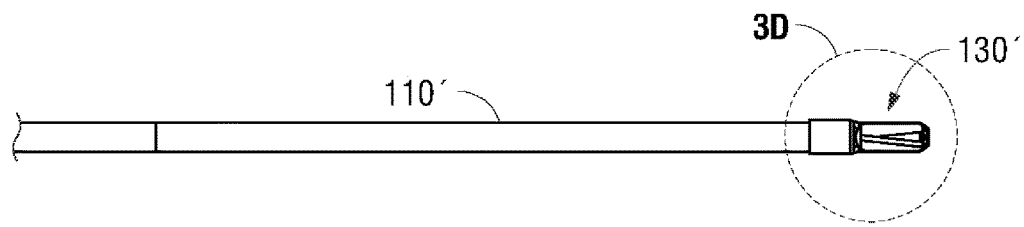
FIG. 3C is a top view of the biopsy tool of FIG. 3A.
Figure 3D:
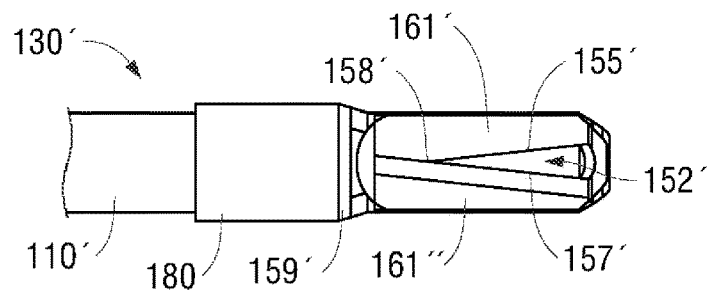
FIG. 3D is an enlarged view of the area of detail of FIG. 3C.

With reference to FIG. 3, rigid distal biopsy member 130 includes a base portion 140, a tissue-receiving portion 150, and a distal end cap 160. Base portion 140 defines a generally cylindrical configuration and houses a sensor 170. Sensor 170, in conjunction with tracking system 70 (FIG. 1), may be employed to enable tracking of biopsy member 130 of biopsy tool 100 as biopsy member 130 is advanced through the patient's airways, as detailed below. Thus, with additional reference to FIG. 1, computer 80, monitoring equipment 60, and/or any other suitable display may be configured to display the three-dimensional model and selected pathway, both of which were generated during the planning phase, along with the current location of sensor 170 of biopsy member 130 to facilitate navigation of biopsy member 130 to the target tissue and/or manipulation of biopsy member 130 relative to the target tissue. Various sensors suitable for use with biopsy member 130 for this purpose are detailed below (see FIGS. 9-11). Alternatively, biopsy tool 100 may not include a sensor and, rather, only LG 92 may be utilized for navigation and positioning. Distal end cap 160 of biopsy member 130 defines a generally blunt configuration. Alternatively, distal end cap 160 may be configured to cut or dissect tissue.

Tissue-receiving portion 150 defines a planar surface 153 and an opening 152 configured to receive a tissue sample therethrough and into the generally hollow interior of biopsy member 130. Opening 152 is defined by first and second longitudinally-extending faces 154, 156. Faces 154, 156 are angled into the interior of tissue-receiving portion 150 and are oriented to define an acute interior angle therebetween, e.g., a generally "V"-shaped configuration. Faces 154, 156 each includes a sharpened cutting edge 155, 157, respectively, disposed on one side of opening 152. Faces 154, 156 are further oriented relative to one another such that edges 155, 157 increasingly approximate one another in the distal to proximal direction, ultimately culminating at an apex point 158 adjacent to proximal shoulder 159. This feature facilitates dynamic tissue cutting, as detailed below. Although generally shown as being formed from a single plate 161, in one embodiment, tissue receiving portion 150 may be defined by two or more plates 161 disposed on base portion 140. It is contemplated that the two or more plates 161 may be arranged in a planar configuration (i.e., side by side), or stacked one over the other as detailed hereinbelow.

With reference to FIGS. 3A-3D, an alternate embodiment of biopsy tool 100 is shown, generally referred to as 100'. In this embodiment, biopsy tool 100' includes a monolithically formed biopsy member 130' that is separate from flexible body 110'. Biopsy member 130' includes a shoulder portion 180 on a proximal end thereof. The shoulder portion 180 defines a cavity therein such that biopsy member 130' may be disposed over the distal end of flexible body 110'. Biopsy member 130' may be fixedly secured to the distal end of flexible body 110' by any suitable means, such as welding, swage fit, adhesives, etc. A base portion 140' defines a cutout such that an opening 152' is formed therein. Opening 152' is configured to receive a tissue sample therethrough and into the generally hollow interior of biopsy member 130'. A pair of plates 161', 161" are disposed on an upper surface of biopsy member 130' in a stacked configuration (see FIG. 3D). Plates 161', 161" may be fixedly secured to biopsy member 130' by any suitable means, such as welding, adhesives, etc. Each of plates 161', 161" defines first and second sharpened cutting edges 155', 157'. Edges 155', 157' are angled into the interior of tissue-receiving portion 152' and are oriented to define an acute interior angle therebetween, e.g., a generally "V"-shaped configuration. Edges 154', 156' are further oriented relative to one another such that edges 155, 157 increasingly approximate one another in the distal to proximal direction, ultimately culminating at an apex point 158' adjacent to proximal shoulder 159'. This feature facilitates dynamic tissue cutting, as detailed below with respect to biopsy member 130.

Referring to FIGS. 1-3, in use, once the planning and navigation phases have been completed, and LG 92 removed from EWC 96, biopsy tool 100 may be inserted through navigation assemblies 90, 91 and bronchoscope 50 to the target tissue. Sensor 170 of biopsy member 130, in conjunction with tracking system 70, as mentioned above, enables tracking of sensor 170 as it is advanced through the patient's airways. Thus, even after biopsy member 130 is extended distally from EWC 96, the position of biopsy member 130 can be tracked, thus permitting navigation of biopsy member 130 to and/or manipulation of biopsy member 130 relative to the target tissue to ensure proper positioning of biopsy member 130 relative to the target tissue and allowing certain tissue structures adjacent the target tissue to be avoided. Details of tracking and navigating using suitable sensors and tracking system 70 will be described in greater detail below, following the description of the various embodiments thereof.

Once biopsy member 130 of biopsy tool 100 is positioned as desired, vacuum source "V" may be activated (e.g., via a syringe, mechanical pump, etc.) to apply suction at opening 152 of tissue-receiving portion 150 of biopsy member 130 to suction tissue into the interior of tissue-receiving portion 150. As a sample of tissue is suctioned through opening 152, the sample begins to be cut away from laterally surrounding tissue via the urging of tissue into contact with edges 155, 157, e.g., as a result of the suction force applied to tissue. Once the tissue sample has been at least partially received within the interior of tissue-receiving portion 150, biopsy member 130 may be translated distally relative to tissue, e.g., via grasping and translating proximal handle portion 120 distally, such that the tissue sample is completely severed from surrounding tissue. This severing of the tissue sample is aided by the relative movement of approximating edges 155, 157 and apex point 158 relative to and through tissue. Upon receiving and fully separating the tissue sample from surrounding tissue, biopsy tool 100 may be withdrawn from the patient's airways and the tissue sample retrieved from biopsy tool 100 for testing. It is also contemplated that multiple samples be taken with biopsy tool 100, e.g., at the same location or various different locations, prior to withdrawal.

Figure 4:
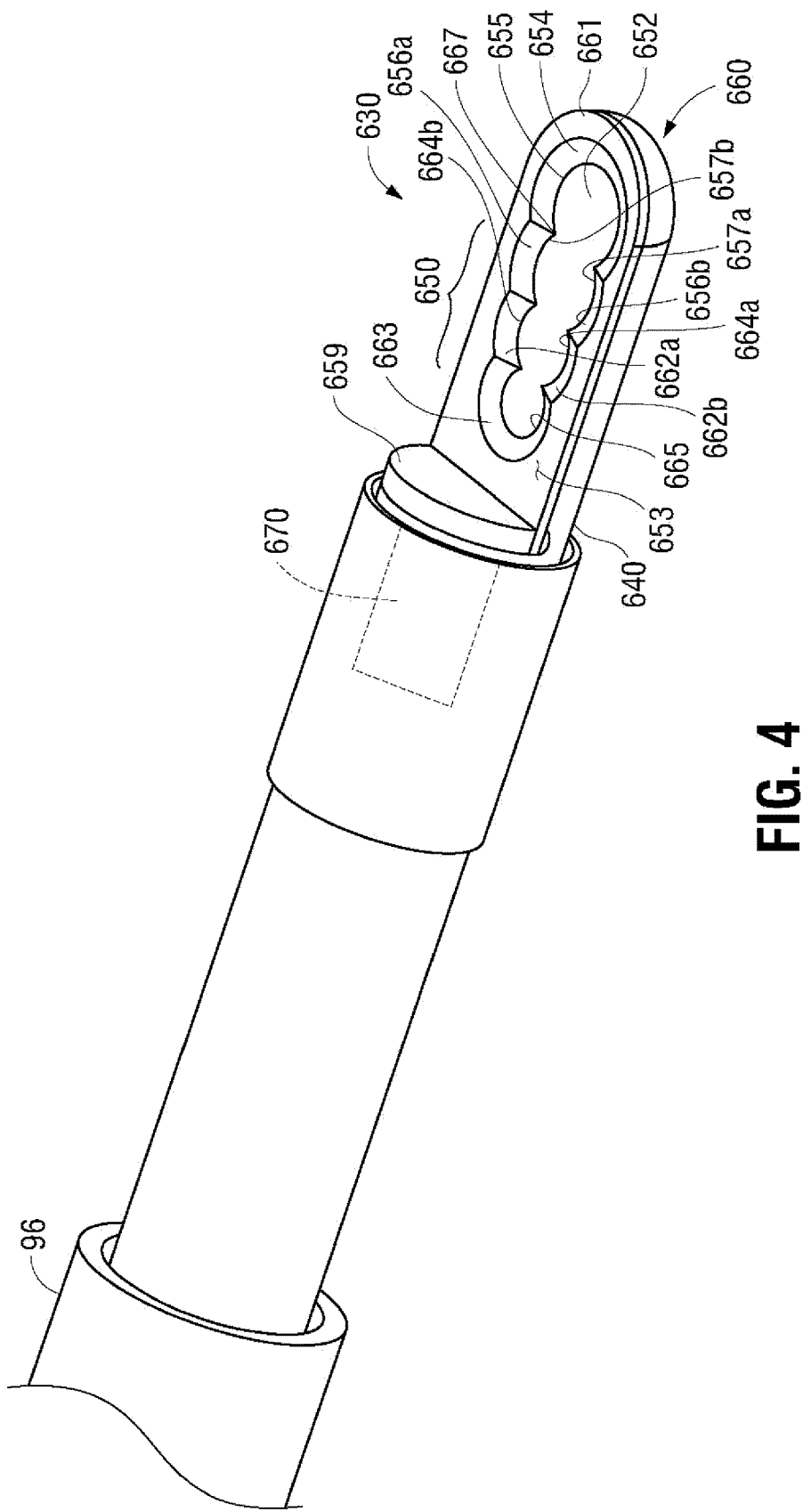
FIG. 4 is a perspective view of the distal end of another biopsy tool provided in accordance with the present disclosure and configured for use with the system of FIG. 1.

Referring now to FIG. 4, another embodiment of a biopsy tool provided in accordance with the present disclosure for obtaining a tissue sample from the target tissue is shown generally identified by reference numeral 630. Similarly as detailed above with respect to the previous embodiment, biopsy tool 630 is configured for use in conjunction with tracking system 70 (FIG. 1) to facilitate navigation of biopsy tool 630 to the target tissue and/or tracking of biopsy tool 630 as it is manipulated relative to the target tissue to obtain the tissue sample.

Biopsy member 630 includes a base portion 640, a tissue-receiving portion 650, and a distal end cap 660. Base portion 640 defines a generally cylindrical configuration and may house a sensor 670. Sensor 670 may be configured similarly to sensor 170 (FIG. 3) and, thus, will not be detailed herein for purposes of brevity. Distal end cap 660 of biopsy member 630 defines a generally blunt configuration. Alternatively, distal end cap 660 may be configured to cut or dissect tissue.

Tissue-receiving portion 650 defines a planar surface 653 and an opening 652 configured to receive tissue therethrough and into the generally hollow interior of biopsy member 630. Opening 652 is defined by a one or more semi-circular faces 654. In one non-limiting embodiment, opening 652 is defined by a series of four interconnecting and overlapping semi-circular faces 654, 656a, 656b, 662a, 662b, and 663. Faces 654, 656a, 656b, 662a, 662b, and 663 are angled into the interior of tissue-receiving portion. Faces 654, 656a, 656b, 662a, 662b, and 663 each includes a sharpened cutting edge 655, 657a, 657b, 664a, 664b, and 665 respectively, disposed on one side of opening 652. Faces 654, 656a, 656b, 662a, 662b, and 663 are further oriented relative to one another such that a plurality of projections 667, extending towards the center of opening 652, are formed at the junction between adjacent faces 654. This feature, in conjunction with sharpened cutting edges 655, 657a, 657b, 664a, 664b, and 665, facilitates dynamic tissue cutting, similarly as detailed above with respect to biopsy member 130 (FIG. 3). In one non-limiting embodiment, tissue receiving portion 650 may be defined by one or more plates 661 disposed between distal end cap 660 and proximal shoulder 659.

Biopsy member 630 may be utilized in a similar respect to biopsy member 130 (FIG. 3) as detailed above, with the exception of the ability to sever the tissue by translating biopsy member 630 proximally or distally relative to the tissue.

Figure 5:
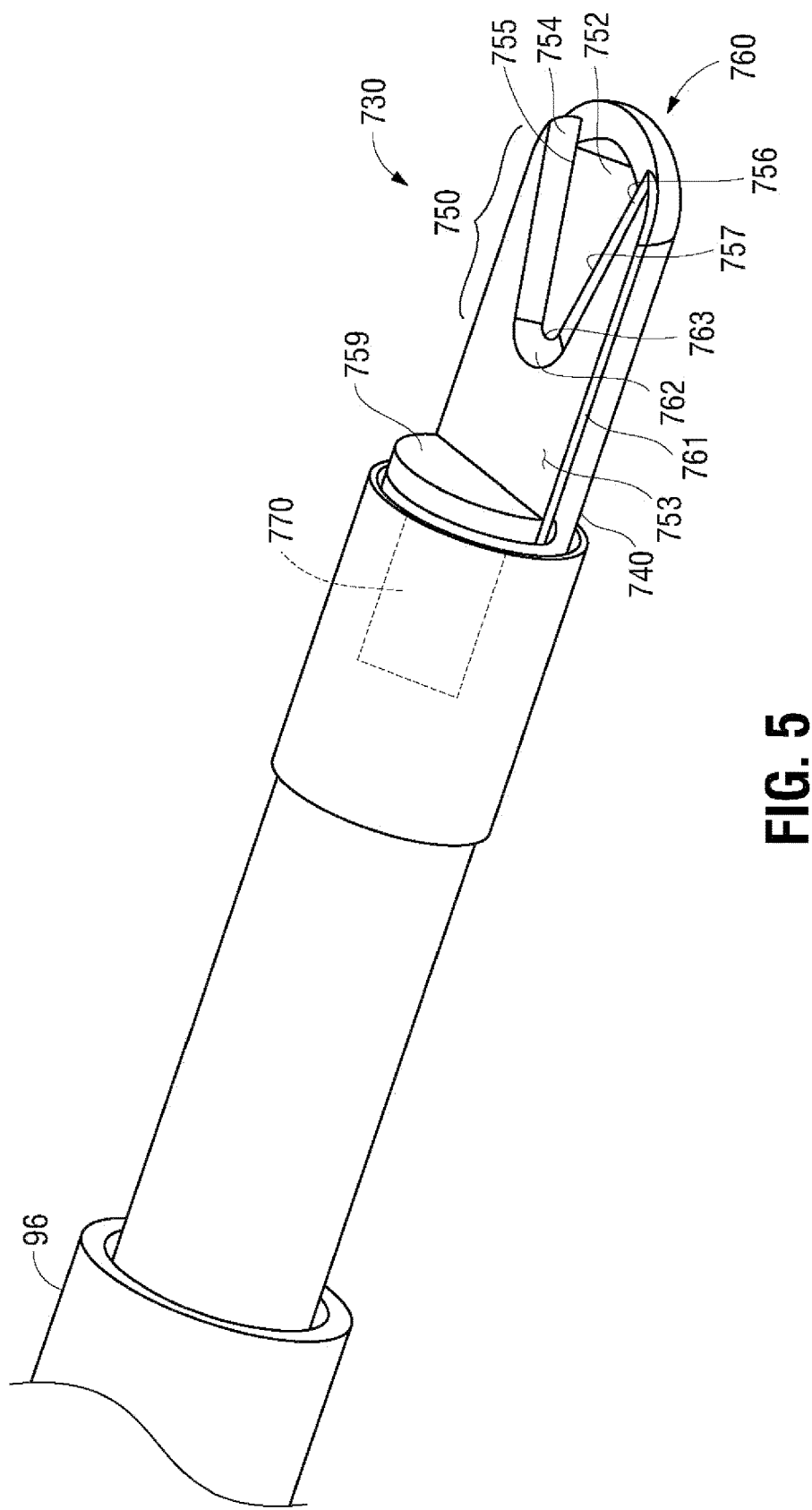
FIG. 5 is a perspective view of the distal end of yet another biopsy tool provided in accordance with the present disclosure and configured for use with the system of FIG. 1.

Referring to FIG. 5, another embodiment of a biopsy tool provided in accordance with the present disclosure for obtaining a tissue sample from the target tissue is shown generally identified by reference numeral 730. Biopsy member 730 includes a base portion 740, a tissue-receiving portion 750, and a distal end cap 760. Base portion 740 defines a generally cylindrical configuration and may houses a sensor 770. Sensor 770 is similar to sensor 170 (FIG. 3) and, thus will not be detailed here for purposes of brevity. Distal end cap 760 of biopsy member 730 defines a generally blunt configuration. Alternatively, distal end cap 760 may be configured to cut or dissect tissue.

Tissue-receiving portion 750 defines a planar surface 753 and an opening 752 configured to receive tissue therethrough and into the generally hollow interior of biopsy member 730. Opening 752 is defined by first and second longitudinally-extending faces 754, 756, and curvate face 762. Faces 754 and 756 are angled into the interior of tissue-receiving portion 750 and are oriented to define an acute interior angle therebetween, e.g., a generally "V"-shaped configuration. Faces 754, 756, and 762 each includes a sharpened cutting edge 755, 757, and 763 respectively, disposed on one side of opening 752, thereby forming a continuous cutting edge capable of cutting tissue. Faces 754 and 756 are further oriented relative to one another such that edges 755 and 757 increasingly approximate one another in the distal to proximal direction, ultimately culminating at radiused cutting edge 763 adjacent to proximal shoulder 759. This feature facilitates dynamic tissue cutting, similarly as detailed above with respect to biopsy member 130 (FIG. 3). In one non-limiting embodiment, tissue receiving portion 750 may be defined by one or more plates 761 disposed between distal end cap 760 and proximal shoulder 759.

Biopsy member 730 may be utilized in a similar respect to biopsy member 130 (FIG. 3) as detailed above to cut tissue.

Figure 6:
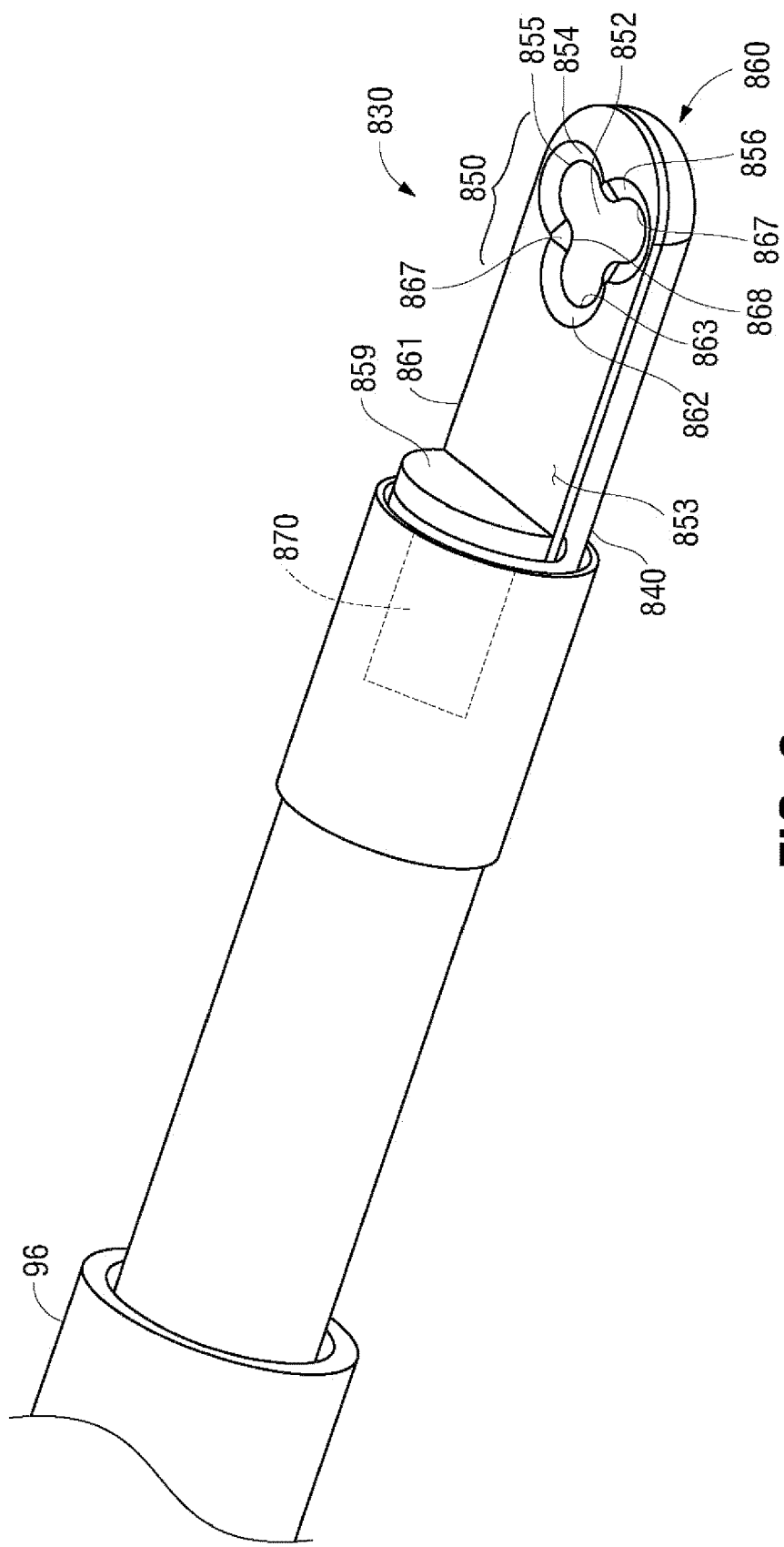
FIG. 6 is a perspective view of the distal end of still another biopsy tool provided in accordance with the present disclosure and configured for use with the system of FIG. 1.

Referring now to FIG. 6, another embodiment of a biopsy tool provided in accordance with the present disclosure for obtaining a tissue sample from the target tissue is shown generally identified by reference numeral 830. Similarly as detailed above with respect to the previous embodiment, biopsy tool 830 is configured for use in conjunction with tracking system 70 (FIG. 1) to facilitate navigation of biopsy tool 830 to the target tissue and/or tracking of biopsy tool 830 as it is manipulated relative to the target tissue to obtain the tissue sample.

Biopsy member 830 includes a base portion 840, a tissue-receiving portion 850, and a distal end cap 860. Base portion 840 defines a generally cylindrical configuration and may house a sensor 870. Sensor 870 may be configured similarly to sensor 170 (FIG. 1) and, thus, will not be detailed herein for purposes of brevity. Distal end cap 860 of biopsy member 830 defines a generally blunt configuration. Alternatively, distal end cap 860 may be configured to cut or dissect tissue.

Tissue-receiving portion 850 defines a planar surface 853 and an opening 852 configured to receive tissue therethrough and into the generally hollow interior of biopsy member 830. Opening 852 is defined by a one or more semi-circular faces 854. In one non-limiting embodiment, opening 852 is defined by a series of interconnecting and overlapping semi-circular faces 854, 856, and 862 arranged in a clover shaped configuration. Faces 854, 856, and 862 are angled into the interior of tissue-receiving portion 850. Faces 854, 856, and 862 each includes a sharpened cutting edge 855, 857, and 863 respectively, disposed on one side of opening 852. Faces 854, 856, and 862 are further oriented relative to one another such that a plurality of projections 867 with cutting edge 868, extending towards the center of opening 852, are formed at the junction between adjacent faces 854, 856, and 862. This feature, in conjunction with sharpened cutting edges 855, 857, and 863, facilitates dynamic tissue cutting, similarly as detailed above with respect to biopsy member 130 (FIG. 3). Although generally shown as being formed from a single plate 861, in other embodiments, tissue receiving portion 850 may be defined by two or more plates 861 disposed on base portion 840.

Biopsy member 830 may be utilized in a similar respect to biopsy member 130 (FIG. 3) as detailed above, with the exception of the ability to sever the tissue by translating biopsy member 830 in any direction (e.g. proximally, distally, laterally, diagonally, etc.) relative to tissue.

Figure 7:
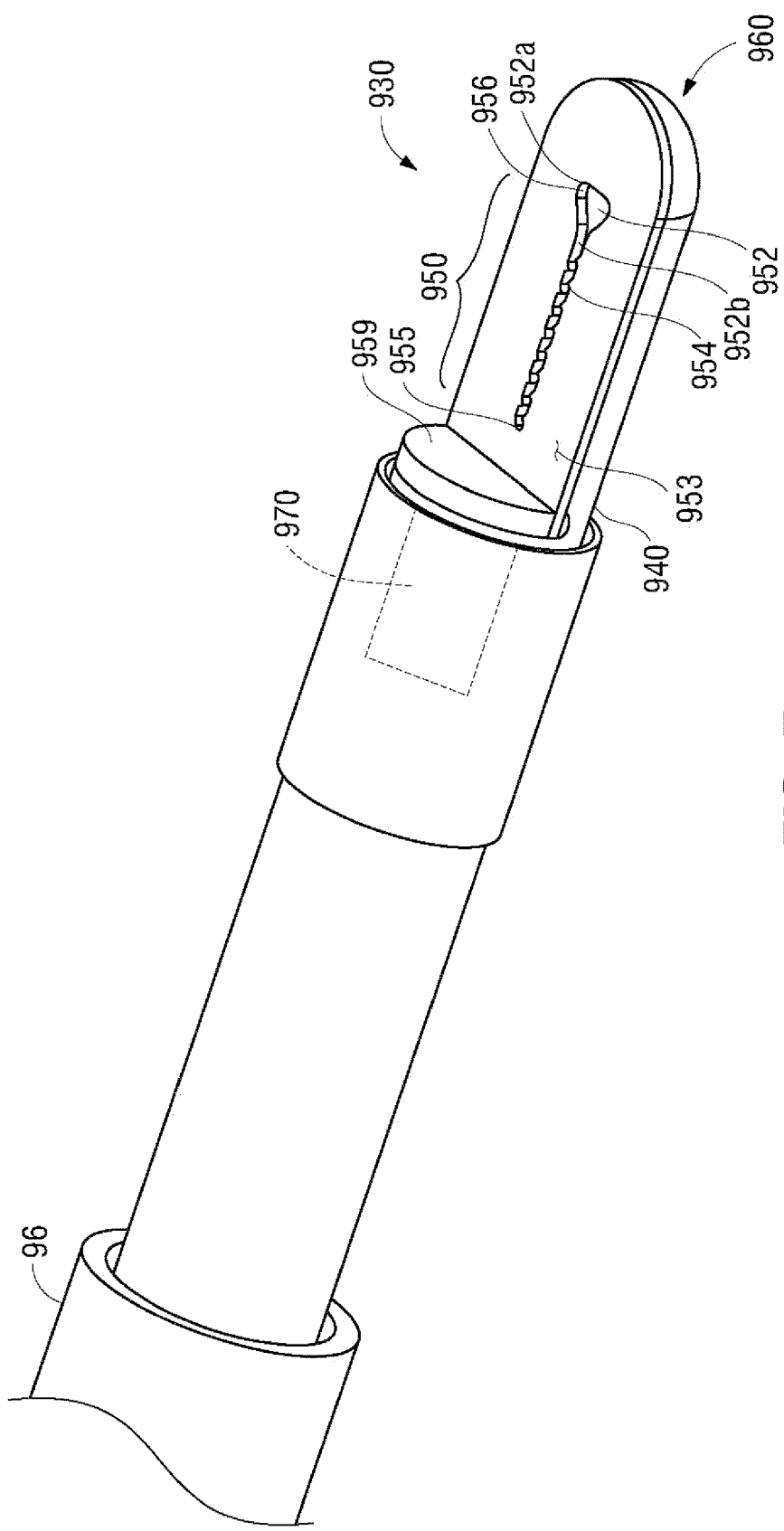
FIG. 7 is a perspective view of the distal end of still yet another biopsy tool provided in accordance with the present disclosure and configured for use with the system of FIG. 1.

Turning to FIG. 7, yet another embodiment of a biopsy tool provided in accordance with the present disclosure for obtaining a tissue sample from the target tissue is shown generally identified by reference numeral 930. Biopsy member 930 includes a base portion 940, a tissue-receiving portion 950, and a distal end cap 960. Base portion 940 defines a generally cylindrical configuration and may house a sensor 970. Sensor 970 is similar to sensor 170 (FIG. 3)

and, thus will not be detailed here for purposes of brevity. Distal end cap 960 of biopsy member 930 defines a generally blunt configuration. Alternatively, distal end cap 960 may be configured to cut or dissect tissue.

Tissue-receiving portion 950 defines a planar surface 953 and an opening 952 configured to receive tissue therethrough and into the generally hollow interior of biopsy member 930. Opening 952 is defined by a distal region having a large opening 952a, including smooth walls 956, tapering proximally to a long narrow opening 952b having a width less than that of large opening 952a and further including a plurality of tines 954 extending towards the center of opening 952. In one non-limiting embodiment, tines 954 may be oriented such that they extend towards the center of opening 952 at an angle such they terminate at a proximal position relative to their base. Large opening 952a may be of any shape, including, but not limited to, triangular, circular, rectangular, or the like. One non-limiting embodiment of large opening 952a is of a triangular configuration. Long narrow opening 952b may include parallel walls or walls forming an acute angle terminating with an apex 955 adjacent to proximal shoulder 959. This feature facilitates dynamic tissue tearing, as detailed below. Although generally shown as being formed from a single plate 961, in other embodiments, tissue receiving portion 950 may be defined by two or more plates 961 disposed on base portion 940.

Biopsy member 930 may be utilized in a similar respect to biopsy member 130 (FIG. 3) as detailed above, with the exception of once biopsy member 930 of biopsy tool 100 is positioned as desired, vacuum source "V" may be activated to apply suction at opening 952 of tissue-receiving portion 950 of biopsy member 930 to suction tissue into the interior of tissue-receiving portion 950. As a sample of tissue is suctioned through opening 952, the sample is trapped within long narrow opening 952b e.g., as a result of the suction force applied to tissue. Once the tissue sample has been at least partially received within the interior of tissue-receiving portion 950, biopsy member 930 may be translated proximally or distally relative to tissue, e.g., via grasping and translating proximal handle portion 120 proximally or distally, such that the tissue sample is completely torn or severed from the surrounding tissue. This tearing of the tissue sample is aided by the plurality of tines 954 which provide a secure grasp on the tissue sample.

Figure 8:
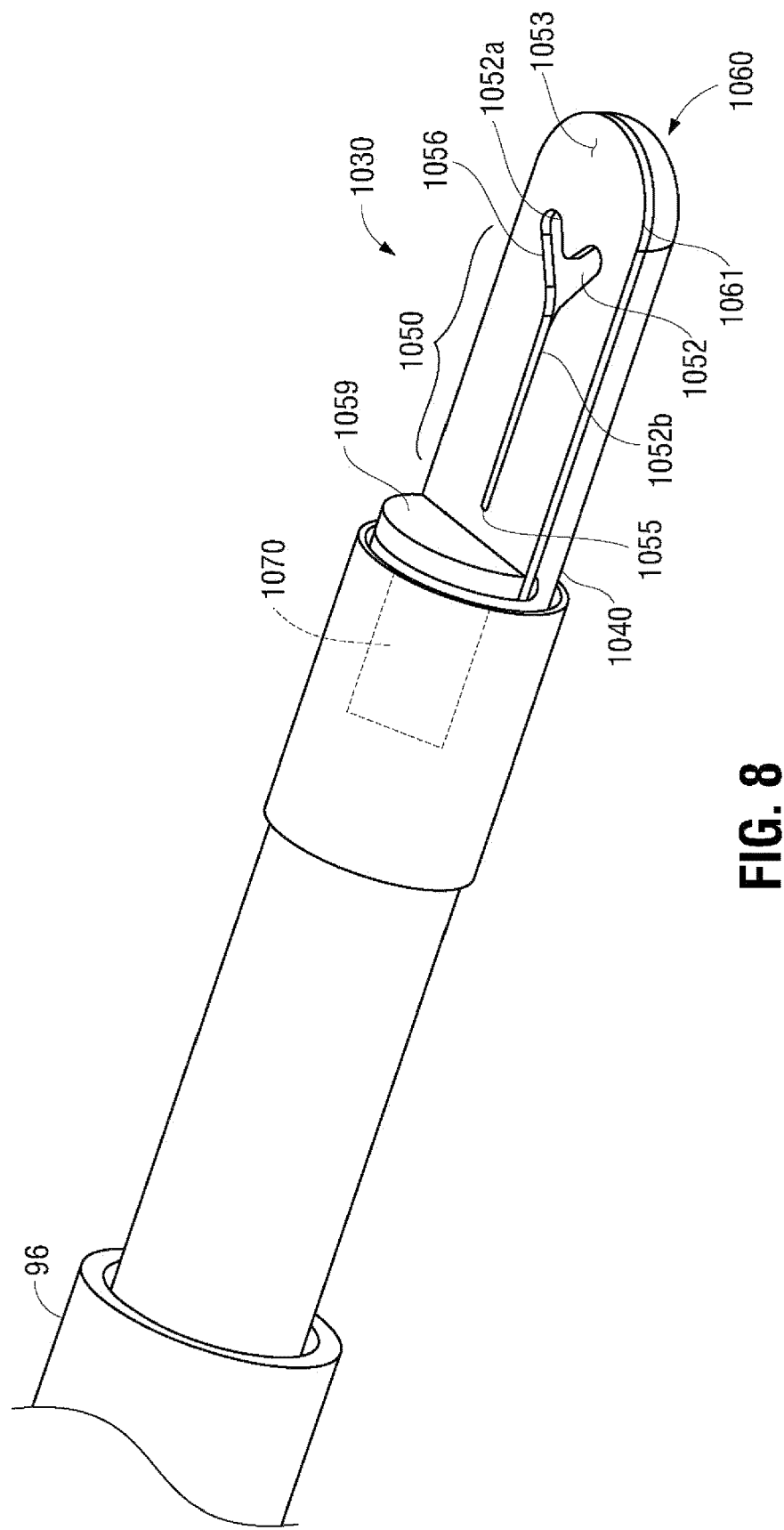
FIG. 8 is a perspective view of the distal end of another biopsy tool provided in accordance with the present disclosure and configured for use with the system of FIG. 1.

Referring now to FIG. 8, yet another embodiment of a biopsy tool provided in accordance with the present disclosure for obtaining a tissue sample from the target tissue is shown generally identified by reference numeral 1030. Biopsy member 1030 includes a base portion 1040, a tissue-receiving portion 1050, and a distal end cap 1060. Base portion 1040 defines a generally cylindrical configuration and may house a sensor 1070. Sensor 1070 is similar to sensor 170 (FIG. 3) and, thus will not be detailed here for purposes of brevity. Distal end cap 1060 of biopsy member 1030 defines a generally blunt configuration. Alternatively, distal end cap 1060 may be configured to cut or dissect tissue.

Tissue-receiving portion 1050 defines a planar surface 1053 and an opening 1052 configured to receive tissue therethrough and into the generally hollow interior of biopsy member 1030. Opening 1052 is defined by a distal region having a large opening 1052a, including smooth walls 1056, tapering proximally to a long narrow opening 1052b having a width less than that of large opening 1052a. Large opening 1052a may be of any shape, including, but not limited to, triangular, circular, rectangular, heart or the like. One non-limiting embodiment of large opening 1052a is of a heart shaped configuration. Long narrow opening 1052b includes walls forming an acute angle terminating with an apex 1055 adjacent to proximal shoulder 1059. This feature facilitates dynamic tissue tearing, similarly as detailed above with respect to biopsy member 930 (FIG. 7). Although generally shown as being formed from a single plate 1061, in one non-limiting embodiment, tissue receiving portion 1050 may be defined by two or more plates 1061 disposed on base portion 1040.

Biopsy member 1030 may be utilized in a similar respect to biopsy member 930 (FIG. 7) as detailed above, with the exception of once biopsy member 1030 of biopsy tool 100 is positioned as desired, vacuum source "V" may be activated to apply suction at opening 1052 of tissue-receiving portion 1050 of biopsy member 1030 to suction tissue into the interior of tissue-receiving portion 1050. As a sample of tissue is suctioned through opening 1052, the sample is trapped within long narrow opening 1052b e.g., as a result of the suction force applied to tissue. Once the tissue sample has been at least partially received within the interior of tissue-receiving portion 1050, biopsy member 1030 may be translated proximally relative to tissue, e.g., via grasping and translating proximal handle portion 120 distally, such that the tissue sample is completely torn or severed from surrounding tissue. This tearing of the tissue sample is aided by the long narrow opening 1052b which provides a secure grasp on the tissue sample.

Figure 9:
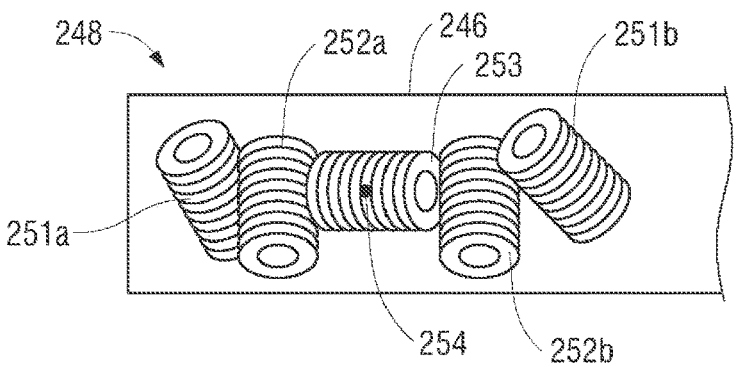
FIG. 9 is a perspective view of a sensor configured for use with any of the biopsy tools of the present disclosure.
Figure 10:
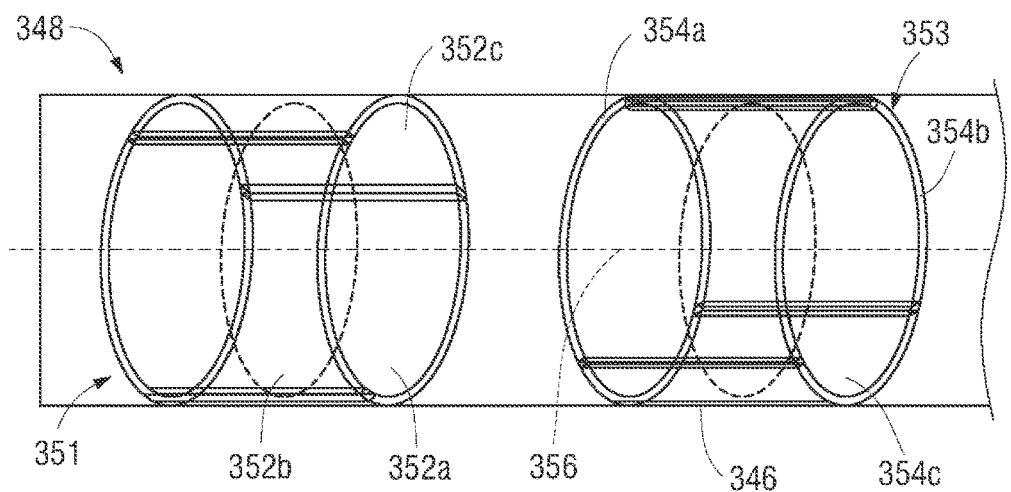
FIG. 10 is a perspective view of another a sensor configured for use with any of the biopsy tools of the present disclosure.
Figure 11:
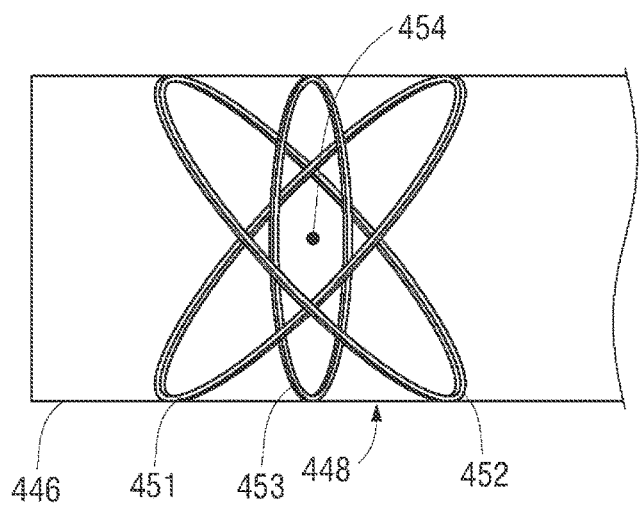
FIG. 11 is a perspective view of yet another sensor configured for use with any of the biopsy tools of the present disclosure.

Turning now to FIGS. 9-11, in conjunction with FIG. 1, various different sensors 248, 348, 448 (FIGS. 9-11, respectively) configured for use as the sensor of any of the biopsy tools detailed herein and/or sensor 94 of LG 92 are described. Although each of the sensors 248, 348, 448 are generally described as employing a plurality of sensor elements, it is contemplated that the sensor of any of the biopsy tools detailed herein and/or sensor 94 of LG 92 may employ any number of sensor elements (e.g., one, two, three, etc.). Therefore, the descriptions to follow should not be construed as limiting, but merely as exemplifications of particular embodiments. Referring to FIG. 9, sensor 248 is shown. Sensor 248 includes a plurality of field component sensor elements 251a, 251b, 1252a, 252b, 253. Each sensor element 251a, 251b, 252a, 252b, 253 is formed as a coil and arranged for sensing a different component of an electromagnetic field generated by transmitter mat 76 (FIG. 12). More specifically, first and second pairs of sensor elements 251a, 251b and 252a, 252b are arranged within sensor housing 246 such that the respective elements 251a, 251b and 252a, 252b of each pair are equidistant from a common reference point 254, while sensor element 253 is centered about reference point 254. Although shown in FIG. 9 as collinearly disposed, other configurations of sensor elements 251a, 251b, 1252a, 252b, 253 are also contemplated. Further, as opposed to providing five sensor elements 251a, 251b, 1252a, 252b, 253 wherein sensor element 253 is centered about the reference point 254, six sensors may be provide, e.g., wherein sensor element 253 is provided as a pair of elements disposed equidistant from reference point 254. The above-described configuration of sensor 248 enables transmitter mat 76 and the plurality of reference sensors 74 (FIG. 1), together with tracking module 72 and computer 80 (FIG. 1), to derive the location of sensor 248 in six degrees of freedom, as detailed below, and as further detailed in U.S. Pat. No. 6,188,355 and published PCT Application Nos. WO 00/10456 and WO 01/67035, previously incorporated herein by reference.

With reference to FIG. 10, sensor 348 is shown including two sensor components 351, 353 arranged within sensor housing 346, each component 351, 353 including three sensor elements 352a, 352b, 352c and 354a, 354b, 354c, respectively. Each sensor element 352a, 352b, 352c and 354a, 354b, 354c is configured as a flat rectangular coil, e.g., including a plurality of turns of conducting wire, bent to define an arcuate shape. As such, the elements 352a, 352b, 352c and 354a, 354b, 354c combine to define first and second generally cylindrical components 351, 353. Components 351, 353 are centered about reference axis 356 and positioned such that each of elements 352a, 352b, 352c and 354a, 354b, 354c are equidistant from reference axis 356 and such that each of elements 352a, 352b, 352c of component 351 are oriented 180 degrees offset as compared to corresponding elements 354a, 354b, 354c, respectively, of component 353. Thus, similarly as with sensor 248 (FIG. 9), sensor 348 enables transmitter mat 76 and the plurality of reference sensors 74 (FIG. 1), together with tracking module 72 and computer 80 (FIG. 1), to derive the location of sensor 348 in six degrees of freedom.

Turning to FIG. 11, sensor 448 includes three coils 451, 452, 453. Coils 451 and 452, 453 are angled relative to housing 446, while coil 453 is circumferentially disposed within housing 446. Coils 451, 452, 453 are oriented to lie in perpendicular planes relative to one another and share a common center reference point 454. By sharing a common center reference point 454, each portion of each coil 451, 452, 453 is equidistant from center reference point 454. Further, this configuration, e.g., wherein coils share a common center reference point 454 rather than being longitudinally displaced relative to one another, allows for the longitudinal dimension of sensor 448 to be minimized. Such a configuration still, however, enables transmitter mat 76 and the plurality of reference sensors 74 (FIG. 1), together with tracking module 72 and computer 80 (FIG. 1), to derive the location of sensor 448 in six degrees of freedom.

Referring additionally to FIG. 1, the electromagnetic waves generated by transmitter mat 76 are received by the various sensor elements of the sensor assembly e.g., the sensor elements of sensors 248, 348, 448 (FIGS. 9-11, respectively) configured for use any of the biopsy tools provided herein or sensor 94 of LG 92, and are converted into electrical signals that are sensed via reference sensors 74. Tracking system 70 further includes reception circuitry (not shown) that has appropriate amplifiers and A/D converters that are utilized to receive the electrical signals from reference sensors 74 and process these signals to determine and record location data of the sensor assembly. Computer 80 may be configured to receive the location data from tracking system 70 and display the current location of the sensor assembly on the three-dimensional model and relative to the selected pathway generated during the planning phase, e.g., on computer 80, monitoring equipment 60, or other suitable display. Thus, navigation of the biopsy tool and/or LG 92 to the target tissue and/or manipulation of the biopsy tool relative to the target tissue, as detailed above, can be readily achieved.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A system for performing a surgical procedure, the system comprising:
    a bronchoscope;
    monitoring equipment coupled to the bronchoscope;
    a tracking system;
    a positioning assembly; and
    a biopsy tool, the biopsy tool including:
        an elongated flexible body extending from a proximal end to a distal end and defining a longitudinal axis therethrough; and
        a biopsy member formed on a distal portion of the elongated flexible body and defining a distal end cap, the distal end cap defining a blunt distal end portion to inhibit the distal end cap from cutting tissue, the biopsy member including a tissue-receiving portion defining an opening disposed perpendicular to the longitudinal axis, the opening defining a plurality of semi-circular faces angled into the interior of the tissue-receiving portion, each face of the plurality of semi-circular faces including sharpened edges capable of cutting tissue.

2. The system of claim 1, wherein the biopsy member includes a sensor assembly including at least one location sensor configured to enable detection of a location of the sensor assembly within a patient's airways.

3. The system of claim 1, further including a computer configured to execute software to facilitate navigation of an extended working channel to a target.

4. The system of claim 1, wherein the biopsy member defines a body separate from the elongated flexible body of the biopsy tool, wherein the biopsy member is secured to the distal end of the elongated flexible body.

5. The system of claim 1, wherein the biopsy member defines a generally hollow interior, the hollow interior in fluid communication with the opening of the tissue receiving portion of the biopsy member.

6. The system of claim 5, wherein the biopsy tool is configured to connect to a vacuum source capable of applying suction at the biopsy member.

7. The system of claim 6, wherein the opening of the tissue receiving portion of the biopsy member is configured to capture tissue of a patient when the vacuum source is applied to the biopsy tool.

8. The system of claim 1, wherein the tracking system includes:
    a tracking module;
    a plurality of reference sensors; and
    a transmitter mat.

9. The system of claim 1, wherein the positioning assembly includes:
    a locatable guide, the locatable guide including a steerable distal tip, wherein a sensor is disposed within the steerable distal tip;
    an extending working channel; and
    a handle;
    wherein the locatable guide and the extended working channel are dimensioned for insertion through a working channel defined through the bronchoscope.

10. A system for performing a surgical procedure, the system comprising:
    a tracking system;

a positioning assembly; and a biopsy tool configured for insertion through a bronchoscope and into a patient's airways, the biopsy tool including:

an elongated flexible body extending from a proximal end to a distal end and defining a longitudinal axis therethrough;

a biopsy member formed on a distal portion of the elongated flexible body and defining a distal end cap, the distal end cap defining a blunt distal end portion to inhibit the distal end cap from cutting tissue, the biopsy member including a tissue-receiving portion defining an opening disposed perpendicular to the longitudinal axis, the opening defining a plurality of semi-circular faces angled into the interior of the tissue-receiving portion, each face of the plurality of semi-circular faces including sharpened edges capable of cutting tissue; and a sensor assembly including at least one location sensor configured to enable detection of a location of the sensor assembly within the patient's airways.

11. The system of claim 10, further including a computer configured to execute software to facilitate navigation of an extended working channel to a target.

12. The system of claim 10, wherein the biopsy member defines a body separate from the elongated flexible body of the biopsy tool, wherein the biopsy member is secured to the distal end of the elongated flexible body.

13. The system of claim 10, wherein the biopsy member defines a generally hollow interior, the hollow interior in fluid communication with the opening of the tissue receiving portion of the biopsy member.

14. The system of claim 13, wherein the biopsy tool is configured to connect to a vacuum source capable of applying suction at the biopsy member.

15. The system of claim 14, wherein the opening of the tissue receiving portion of the biopsy member is configured to capture tissue of a patient when the vacuum source is applied to the biopsy tool.

16. A system for performing a surgical procedure, the system comprising:

a bronchoscope;

a tracking system including a tracking module, a plurality of reference sensors, and a transmitter mat; and a biopsy tool configured for insertion through the bronchoscope and into a patient's airways, the biopsy tool including:

an elongated flexible body extending from a proximal end to a distal end and defining a longitudinal axis therethrough; and a biopsy member formed on a distal portion of the elongated flexible body and defining a distal end cap, the distal end cap defining a blunt distal end portion to inhibit the distal end cap from cutting tissue, the biopsy member including a tissue-receiving portion defining an opening disposed perpendicular to the longitudinal axis, the opening defining a plurality of semi-circular faces angled into the interior of the tissue-receiving portion, each face of the plurality of semi-circular faces including sharpened edges capable of cutting tissue.

17. They system of claim 16, wherein the biopsy member includes a sensor assembly including at least one location sensor configured to enable detection of a location of the sensor assembly within the patient's airways.

18. The system of claim 16, further including a computer configured to execute software to facilitate navigation of an extended working channel to a target.

19. The system of claim 16, wherein the biopsy member defines a body separate from the elongated flexible body of the biopsy tool, wherein the biopsy member is secured to the distal end of the elongated flexible body.

20. The system of claim 16, wherein the biopsy member defines a generally hollow interior, the hollow interior in fluid communication with the opening of the tissue receiving portion of the biopsy member.

* * * * *